(12) United States Patent
Bonnin et al.

(10) Patent No.: US 10,042,184 B2
(45) Date of Patent: Aug. 7, 2018

(54) METHOD FOR IMPROVING VISUAL COMFORT TO A WEARER AND ASSOCIATED ACTIVE SYSTEM OF VISION

(71) Applicant: Essilor International, Charenton-le-Pont (FR)

(72) Inventors: Thierry Bonnin, Charenton-le-Pont (FR); Guillaume Giraudet, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 0 days.

(21) Appl. No.: 14/433,340

(22) PCT Filed: Oct. 7, 2013

(86) PCT No.: PCT/EP2013/070781
§ 371 (c)(1),
(2) Date: Apr. 2, 2015

(87) PCT Pub. No.: WO2014/053658
PCT Pub. Date: Apr. 10, 2014

(65) Prior Publication Data
US 2015/0241717 A1 Aug. 27, 2015

(30) Foreign Application Priority Data
Oct. 5, 2012 (EP) .................... 12306221

(51) Int. Cl.
*A61B 3/113* (2006.01)
*G02C 7/10* (2006.01)
*G02C 7/16* (2006.01)

(52) U.S. Cl.
CPC .............. *G02C 7/101* (2013.01); *A61B 3/113* (2013.01); *G02C 7/16* (2013.01); *G02C 2202/10* (2013.01)

(58) Field of Classification Search
CPC . G02C 7/16; G02C 7/10; G02C 5/001; G02C 9/02; G02C 9/04; G02C 7/101; G02C 2202/10; A61B 3/113
(Continued)

(56) References Cited

U.S. PATENT DOCUMENTS

| 4,106,217 A | 8/1978 | Witt |
| 5,422,690 A * | 6/1995 | Rothberg ............... A61B 3/112 351/209 |

(Continued)

FOREIGN PATENT DOCUMENTS

| WO | WO 92/10130 | 6/1992 |
| WO | WO 2010/130931 | 11/2010 |

(Continued)

*Primary Examiner* — William R Alexander
*Assistant Examiner* — Henry Duong
(74) *Attorney, Agent, or Firm* — Oblon, McClelland, Maier & Neustadt, L.L.P.

(57) ABSTRACT

Active vision system comprising: first and second customizable ophthalmic lenses (22) having an electrically variable occultation between substantially transparent and substantially obscured states; identification device (32) adapted for identifying whether the wearer's viewing state is in a near vision viewing state when wearing the customizable ophthalmic lenses; and processor (40) configured to: switch the electrically variable occultation of one of the customizable ophthalmic lenses (22) from the first to the second light occultation states when a near vision viewing state (NVVS) is identified by the identification device while at the same time the other lens is in the transparent state; and control the electrically variable occultation of the customizable ophthalmic lenses (22) such that they are in the first light occultation state when the wearer's viewing state is identified as being different from a near vision viewing state (NVVS) by identification device (32).

14 Claims, 4 Drawing Sheets

(58) Field of Classification Search
USPC .......................................................... 351/45
See application file for complete search history.

(56) References Cited

U.S. PATENT DOCUMENTS

| | | | |
|---|---|---|---|
| 5,841,507 A | 11/1998 | Barnes | |
| 2008/0055541 A1 | 3/2008 | Coulter et al. | |
| 2008/0170203 A1* | 7/2008 | Esser | G02C 7/085 |
| | | | 351/159.75 |
| 2011/0250962 A1* | 10/2011 | Feiner | A63F 13/06 |
| | | | 463/31 |
| 2012/0050681 A1 | 3/2012 | Bonnin | |
| 2012/0050682 A1 | 3/2012 | Bonnin | |
| 2012/0081666 A1* | 4/2012 | Kiderman | A61B 3/113 |
| | | | 351/210 |
| 2013/0021456 A1* | 1/2013 | Inoue | A61B 3/10 |
| | | | 348/51 |
| 2015/0334658 A1* | 11/2015 | Kulas | H04W 52/0254 |
| | | | 455/566 |

FOREIGN PATENT DOCUMENTS

| | | |
|---|---|---|
| WO | WO 2010/130932 | 11/2010 |
| WO | WO 2012/036638 | 3/2012 |

\* cited by examiner

METHOD FOR IMPROVING VISUAL COMFORT TO A WEARER AND ASSOCIATED ACTIVE SYSTEM OF VISION

RELATED APPLICATIONS

This is a U.S. national stage under 35 USC § 371 of application No. PCT/EP2013/070781, filed on Oct. 7, 2013. This application claims the priority of European application no. 12306221.8 filed Oct. 5, 2012, the entire content of which is hereby incorporated by reference.

FIELD OF THE INVENTION

The invention relates to a method for improving visual comfort to a wearer and to an active system of vision adapted to carry out the steps of the method.

The invention further relates to a computer program product and a computer readable medium.

BACKGROUND OF THE INVENTION

The invention relates to the field of active optical elements, in particular to carry out an ophthalmic lens. The optical element is suitable to be in a transparent state.

Within the meaning of the invention, an optical element is transparent when an object that is located on a first side of the optical element can be viewed without significant loss of contrast by an observer who is himself across the optical element. The object and the observer are each located at distance of the optical element. In other words, an image of the object is formed through the optical element with no significant loss of quality of visual perception for the observer, also called "the wearer".

The optical element is suitable to be at least partially obscured, i.e. in a state unsuitable for reading. Within the meaning of the present invention, "an optical element obscured" means that the image of an object formed through the optical element is indistinct or hidden from view of the wearer. For example, the obscuration is achieved by occultation of at least a part of the lens. Occultation refers to limitation of the visual information entering in the eye, quantitatively, for example by light darkening/blocking and/or light reflecting and/or to alteration of visual information entering in the eye, qualitatively, for example by light defocusing and/or light scattering.

It is known to use substances having specific optical properties to make active transparent optical elements. These substances cooperate to give optical characteristics required for a particular application to the optical component.

Nevertheless, people presenting binocular problems in near vision still have low visual comfort in near vision with actual spectacle lenses. For example, these people can have an insufficiency of convergence, phoric anomalies, anisometropia, dyslexia, or other problems being able to be at the origin of maladjustment to the actual lenses for example.

SUMMARY OF THE INVENTION

One aim of the present invention is to provide a method for customizing an active system of vision with enhanced visual comfort for the wearer, particularly during reading activity, and which is suitable to take into account varying viewing conditions that can be encountered for example in everyday life.

To achieve this, one aspect of the invention is directed to a method for improving visual comfort of a wearer comprising the following steps:
 providing a first and a second customizable ophthalmic lenses mounted on a spectacle frame, the first customizable ophthalmic lens being adapted to be disposed in front of one eye of the wearer and the second customizable ophthalmic lens being adapted to be disposed in front of the other eye of the wearer, each lens having an electrically variable occultation between a first light occultation state and a second light occultation state, the first light occultation state being substantially transparent and the second light occultation state being substantially obscured;
 identifying the wearer's viewing state among at least a near vision viewing state, a near vision viewing state being defined for viewing distances equal to or lower than 60 cm;
 switching the electrically variable occultation of one of the first and the second customizable ophthalmic lenses from the first light occultation state to the second light occultation state when a near vision viewing state is identified while at the same time the other lens is in the transparent state; and
 providing the first and the second customizable ophthalmic lenses such that each of their electrically variable occultation is in the first light occultation state when the wearer's viewing state is identified as being different from said near vision viewing state.

In the frame of the present invention, the wording "customizable lens" is used to designate a lens whose dioptric function can be modified according to the wearer's needs.

In the frame of the present invention, the wording "a lens having an electrically variable occultation" is used to designate a lens which has an electrically variable transfer function adapted to cause the disappearing of an object from wearer's view, for example by light darkening/blocking, light defocusing, light reflecting and/or light scattering.

Of course, only one of the first and the second customizable ophthalmic lenses is switched from the first light occultation state to the second light occultation state at a time when a near vision viewing state is identified while at the same time the other lens is in the transparent state. Thus, only one eye is occluded during a near vision state at a time. Nevertheless, according to others embodiments, the other or second eye can be occluded during the same near vision state or during another near vision state but not at the same time as the previous or first eye which would then return in the transparent state. Also, there is always only one eye occluded at a time during the near vision states but not necessarily always the same eye.

Furthermore, the electrically variable occultation of the first and the second customizable ophthalmic lenses from the first light occultation state to the second light occultation state can be switched alternatively, periodically or not, during a same or different near vision states.

Thanks to the present invention, it is now possible to improve visual performance of a wearer by providing a method and associated system of nonpermanent occlusion of one eye of the wearer during a near-vision activity, like reading. Indeed, the occlusion of one eye allows an enhanced stability of fixing a point when reading to the wearer.

Moreover, the transparency of the associated system of nonpermanent occlusion according to the invention is not decreased too much for a standard use in interior, in average and weak luminous environment and for the reading on the contrary to existing system of monocular occlusion wherein a single lens is occluded by covering it with opaque tape or patch.

According to an embodiment, the method is implemented by technical means, as for example by computer means controlling such a device.

According to another embodiment the method further comprises the following steps consisting of:
- identifying which one of the first and the second customizable ophthalmic lenses has its electrically variable occultation switched from the first light occultation state to the second light occultation state; and
- switching the electrically variable occultation of the other lens from the first light occultation state to the second light occultation state when a further near vision viewing state is identified.

Thanks to this embodiment, it is now possible to alternate which eye is occluded during near-vision viewing state.

According to another embodiment that can be combined with the previous ones, according to all the possible combinations, the method further comprises the following steps when a near vision viewing state is identified:
- providing a switching time period; and
- switching alternatively after each switching time period, the electrically variable occultation of the first and the second customizable ophthalmic lenses from the first light occultation state to the second light occultation state during a near vision viewing state.

According to another embodiment that can be combined with the previous ones, according to all the possible combinations, the step for identifying the wearer's viewing state comprises steps for measuring an oculo-motor activity of each eye of the wearer and comparing measured oculo-motor activity of each eye of the wearer with standard oculo-motor activity of each eye during a near vision viewing state.

According to a subembodiment, the step for identifying the wearer's viewing state comprises steps for:
- determining, for each eye, the actual gaze direction of the eye of the wearer when wearing the first and the second customizable ophthalmic lenses;
- determining the number and magnitude of ocular saccades for each eye from the actual gaze directions of the eyes of the wearer; and
- comparing the actual number and magnitude of ocular saccades of the eyes of the wearer with standard number and magnitude of ocular saccades during a near vision viewing state.

The ocular saccades can be horizontal ocular saccades.

According to another embodiment that can be combined with the previous ones, according to all the possible combinations, the step for identifying the wearer's viewing state comprises steps for:
- determining, for each eye, the actual gaze direction of the eye of the wearer when wearing the first and the second customizable ophthalmic lenses;
- determining a convergence of the eyes of the wearer from the actual gaze directions of the eyes of the wearer; and
- comparing the actual convergence of the eyes of the wearer with a standard viewing convergence of the eye during a near vision viewing state.

According to another embodiment that can be combined with the previous ones, according to all the possible combinations, the step for identifying the wearer's viewing state comprises steps for measuring the actual viewing distance of the wearer when wearing the customizable ophthalmic lens, and for comparing the actual viewing distance of the wearer with a standard viewing distance during a near vision viewing state.

According to another embodiment that can be combined with the previous ones, according to all the possible combinations, the step for identifying the wearer's viewing state comprises steps for measuring the actual inclination of the head of the wearer when wearing the customizable ophthalmic lens, and for comparing the actual inclination of the head of the wearer with a standard viewing inclination of the head during a near vision viewing state.

According to another embodiment that can be combined with the previous ones, according to all the possible combinations, the obscuration of the second light occultation state is achieved by light blocking, light defocusing and/or light scattering.

Furthermore, another aspect of the invention relates to a computer program product comprising one or more stored sequences of instructions that is accessible to a processor and which, when executed by the processor, causes the processor to carry out the steps of the different embodiments of the preceding method.

Another aspect of the invention relates to a computer readable medium storing one or more sequences of instructions of the preceding computer program product.

Another aspect of the invention relates to an active system of vision for a wearer comprising:
- a first and a second customizable ophthalmic lenses mounted on a spectacle frame, the first customizable ophthalmic lens being adapted to be disposed in front of one eye of the wearer and the second customizable ophthalmic lens being adapted to be disposed in front of the other eye of the wearer, each lens having an electrically variable occultation between a first light occultation state and a second light occultation state, the first light occultation state being substantially transparent and the second light occultation state being substantially obscured;
- an identification device adapted for identifying the wearer's viewing state among a near vision viewing state when wearing the first and the second customizable ophthalmic lenses, a near vision viewing state being defined for viewing distances equal to or lower than 60 cm; and
- a processor operatively connected to each of the first and the second customizable ophthalmic lenses and to the identification device, wherein the processor is configured to:
  - switch the electrically variable occultation of one of the first and the second customizable ophthalmic lenses from the first light occultation state to the second light occultation state when a near vision viewing state is identified by the identification device while at the same time the other lens is in the transparent state; and
  - control the electrically variable occultation of the first and the second customizable ophthalmic lenses such that they are in the first light occultation state when the wearer's viewing state is identified as being different from said near vision viewing state by the identification device.

The system is therefore light and very compact because it is in the form of spectacles. It can be used in everyday life, even when the user encompasses different successive viewing conditions. In particular, a person wearing a pair of spectacles of the invention retains complete freedom of movement with good viewing ability.

According to an embodiment, the active system of vision is adapted for carried out the steps of the previous method whatever the embodiment of the method according to the invention.

According to various embodiments that can be combined according to all the possible combinations:

the first and the second customizable ophthalmic lenses having an electrically variable occultation comprising a layer chosen from the list consisting of polymer dispersed liquid crystals, nematic liquid crystals, or cholesteric liquid crystals.

wherein each of the first and the second customizable ophthalmic lenses comprises a transparent set of electroactive cells juxtaposed parallel to a surface of the said customizable ophthalmic lens, said set of cells being suitable for providing an optical phase-shift distribution function with a constant value within each cell, the optical phase-shift distribution being associated to the electrically variable occultation of said customizable ophthalmic lens and wherein the processor is configured to:

calculate a modified phase-shift distribution function for each customizable ophthalmic lens such that the modified phase-shift distribution function is associated to the in the second light occultation state of the electrically variable occultation; and activate each electroactive cells according to the said modified phase-shift distribution function.

the first and the second customizable ophthalmic lenses are adapted to provide optical power for visual corrections of the wearer; and the detection device is disposed on a face of the first and the second customizable ophthalmic lenses facing the eye.

An active system of vision according to the invention can advantageously be used by people presenting binocular problems in near vision like people having an insufficiency of convergence, phoric anomalies, anisometropia, dyslexia or other problems being able to be at the origin of maladjustment to the multifocal lenses.

BRIEF DESCRIPTION OF THE DRAWINGS

Further features and advantages of the invention will appear from the following description of embodiments of the invention, given as non-limiting examples, with reference to the accompanying drawings listed hereunder.

For clarity, the dimensions of the elements represented in these figures are not in proportion to the actual dimensions, nor to the ratios of the actual dimensions. In addition, identical references in the different figures denote identical elements or elements with identical functions.

DETAILED DESCRIPTION OF THE INVENTION

The invention relates to a method and an associated system, for improving visual comfort to a wearer according to wearer's optical needs and wearer's prescription data if necessary.

For instance, the wearer's optical needs are to have an ophthalmic lens suitable for specific applications as reading, computer activity, stairs climbing, reading in bed for seniors, limiting ocular tiredness, do-it-yourself activity.

The present invention applies for all kind of spectacle lenses: single vision, bifocal or progressive addition lenses.

Before further detailing the method improving visual comfort to a wearer according to the invention, several terms used in the remainder of the description will be defined below.

Figure 1:
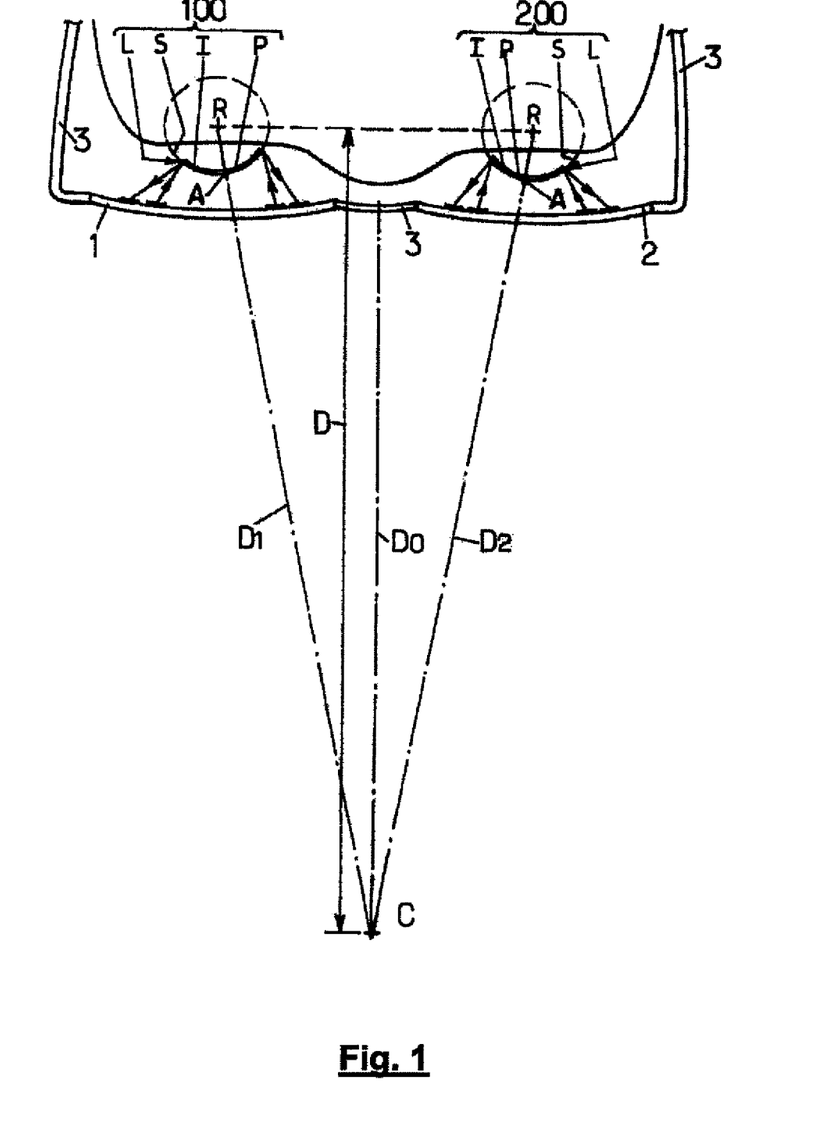
FIG. 1 illustrates a plan view showing the use of a pair of spectacles.

With reference to FIG. 1, a pair of spectacles comprises a frame 3 and two ophthalmic lenses, respectively denoted 1 and 2 for the right and left lens. The frame 3 holds the lenses 1 and 2 in relative fixed positions, and allows placing them in front of the eyes of the wearer in a manner which remains substantially constant during successive periods of use. The lenses 1 and 2 can be permanently assembled into the frame 3 using one of the assembly methods known to opticians.

The references 100 and 200 denote the wearer's eyes, 100 indicating the right eye and 200 indicating the left eye. For each of the wearer's eyes 100, 200, the references S, I, P, L and R denote respectively the sclera, the iris, the pupil, the limbus, and the center of rotation of the eye. It is known that the iris I is a circular ring having an inner diameter which is variable and which determines the size of the pupil P, and a constant outer diameter. The limbus L is the outside border of the iris L, between the iris and the sclera S. It is therefore a circle of constant size which is fixed relative to the corresponding eye when the eye is turning around its center of rotation R. Visually, the limbus L is the circular border between the white sclera S and the colored iris I.

Figure 2:
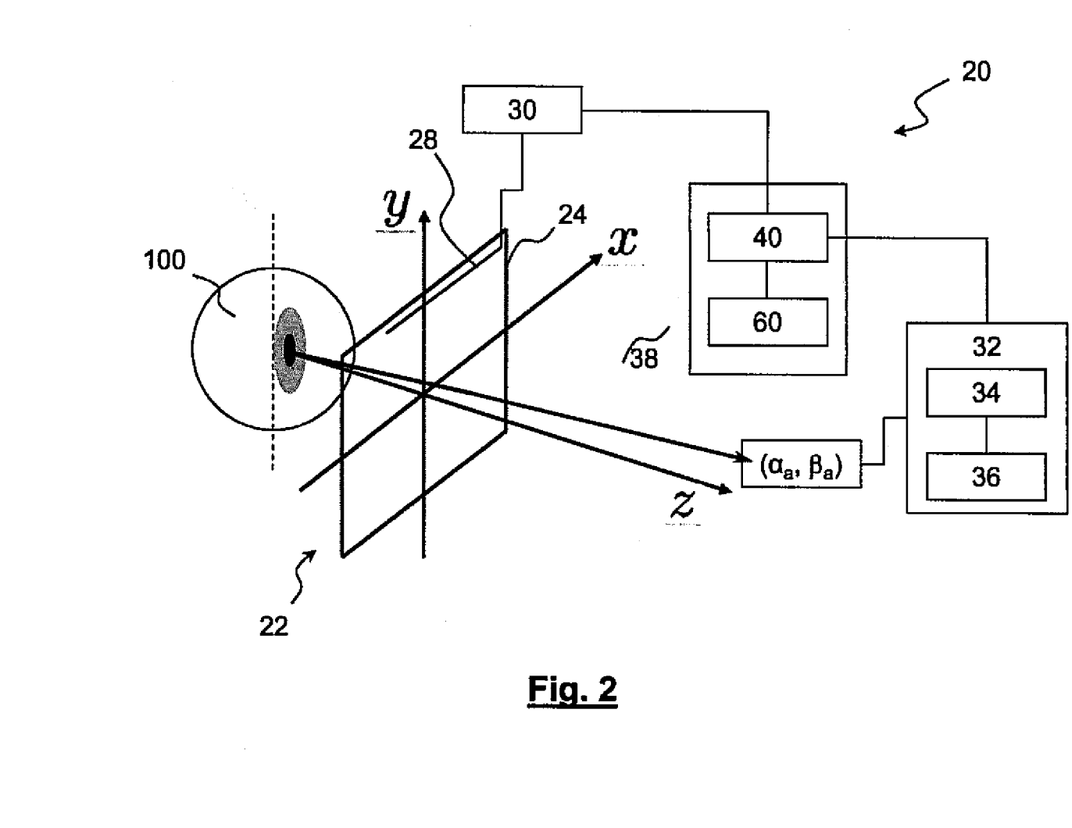
FIG. 2 is a schematic representation of an active system of vision according to an embodiment of the invention.

For each eye 100, 200, the respective axis D1, D2 which passes through the center of rotation R and the center A of the corresponding pupil P is the optical axis of that eye. The center A of the pupil P is also the apex of the crystalline lens. The optical axis D1, D2, is fixed relative to the respective eye 100, 200, such that it rotates with the limbus L. The optical axes D1 and D2 of the eyes 100 and 200 converge to a common point C, which is called the point of convergence of the eyes and which is the location of a virtual object being viewed by the wearer at a given moment. The average direction D0 of the optical axes D1 and D2 is the direction of gaze of the wearer at that moment. Usually, the direction of gaze D0 connects a midpoint of the segment between the two eyes' centers of rotation R and the point of convergence C. The observation distance, which is denoted D in FIG. 2, is the distance of the point of convergence C relative to the centers of rotation R.

Specific embodiments of the method according to the invention are based on the determination of the direction of gaze D0 relatively to the face of the wearer. To achieve this, a method for determining the direction of gaze of a wearer is carried out. For example, WO 2010/130932 A1 proposes such method for determining the direction of gaze of a wearer.

In WO 2010/130932 A1, the direction of gaze D0 is determined by detecting the rotational position of each eye 100, 200 relative to the corresponding lens 1, 2. Thus each lens 1, 2 according to WO 2010/130932 A1 allows determining the angular position of the optical axis D1, D2 of the corresponding eye 100, 200. The direction of gaze D0 of the wearer is then deduced from the respective positions of the two optical axes D1 and D2.

Other specific embodiments of the method according to the invention are based on the determination of a convergence of the eyes of the wearer. To achieve this, a method for determining the convergence of the eyes of the wearer is carried out. For example, WO 2010/130931 A1 proposes such method for determining a convergence of the eyes of the wearer.

In WO 2010/130931 A1, the position of the point of convergence C is determined by detecting the rotational position of each eye 100, 200 relative to the corresponding lens 1, 2. Thus each lens 1, 2 according to WO 2010/130931 A1 allows determining the angular position of the optical axis D1, D2 of the corresponding eye 100, 200. The point of convergence C, with the observation distance D if necessary, is then deduced from the respective positions of the two optical axis D1 and D2.

To define the position of the optical axis of each eye, two angles are used, $\alpha$ and $\beta$, respectively called the elevation and eccentricity. The elevation $\alpha$ is usually identical for both eyes 100 and 200, and is the angle between each optical axis D1 or D2 and a reference plane which is horizontal when the wearer's head is vertical. The elevation value for the direction of gaze D0 is then also equal to this common value.

The eccentricity $\beta$ of the optical axis D1 or D2 of each eye is the angle between this axis and a median plane of the face, which is vertical when the wearer's head is vertical. The eccentricity $\beta$ can be considered as positive in the direction of the wearer's nose for each eye, and generally has absolute values which are distinct for the two eyes at the same moment. The difference between these two absolute values determines the convergence of the eyes, meaning the observation distance D. The azimuth value for the direction of gaze D0 is equal to half the difference of the respective eccentricity values for the two eyes, using the orientation convention of eccentricity angles just indicated.

In practice, the elevation and eccentricity of the optical axis D1, D2 of each eye 100, 200 may be determined based on the position of the limbus L of that eye.

A given gaze direction corresponds to a couple ($\alpha$, $\beta$).

It is well-known by the man skilled in the art to define dioptric function $DF(\alpha, \beta)$ adapted to correct visual defects of the wearer in this reference system of coordinates ($\alpha$, $\beta$), i.e. according to each gaze direction of the wearer.

In the remainder of the description, terms like «up», «bottom», «horizontal», «vertical», «above», «below », or other words indicating relative position may be used. These terms are to be understood in the wearing conditions of the lens. Notably, the "upper" part of the lens corresponds to a negative lowering angle $\alpha<0°$ and the "lower" part of the lens corresponds to a positive lowering angle $\alpha>0°$.

Now, an active vision system for a wearer according to the invention will be described in details with reference to FIG. 2.

The active system of vision 20 for the wearer comprises a first and a second customizable ophthalmic lenses 22, each mounted on a spectacle frame. For simplicity, only one customizable ophthalmic lens is illustrated. The first customizable ophthalmic lens 22 is adapted to be disposed in front of one eye of the wearer and the second customizable ophthalmic lens is adapted to be disposed in front of the other eye of the wearer.

The first customizable ophthalmic lens 22 has an electrically variable occultation $T_1$ between a first light occultation state $T_{1,a}$ and a second light occultation state $T_{1,b}$. The first light occultation state $T_{1,a}$ of the electrically variable occultation $T_1$ is substantially transparent and the second light occultation state $T_{1,b}$ of the electrically variable occultation $T_1$ is substantially obscured.

The second customizable ophthalmic lens has an electrically variable occultation $T_2$ between a first light occultation state $T_{2,a}$ and a second light occultation state $T_{2,b}$. The first light occultation state $T_{2,a}$ of the electrically variable occultation $T_2$ is substantially transparent and the second light occultation state $T_{2,b}$ of the electrically variable occultation $T_2$ is substantially obscured.

The obscuration of the second light occultation state $T_{1,b}$, $T_{2,b}$ is achieved by light darkening/blocking, light defocusing, light reflecting and/or light scattering.

The term obscuration by light darkening/blocking and/or by light reflecting should be taken to mean that less than 50% of incident light is transmitted to each eye and preferably less than 20% of incident light is transmitted to each eye.

In a preferred embodiment, less than 10% of incident light is transmitted to each eye by a lens occulted by light darkening/blocking and/or by light reflecting.

The term obscuration by light defocusing and/or by light scattering should be taken to mean that maximal visual acuity of the wearer is decreased of at least 50% and preferably at least 80%. Visual acuity refers to acuteness or clearness of vision, which is dependent on the sharpness of the retinal focus within the eye and the sensitivity of the interpretative faculty of the brain. It is well-known that visual acuity is a measure of the spatial resolution of the visual processing system.

To achieve this, the first and the second customizable ophthalmic lenses 22 having an electrically variable occultation comprise each a layer made of an active electro-material such that the refraction index of the customizable ophthalmic lens can vary in each lens independently from each other under the action of an electric field induced by individual electrodes 28.

Of course, the active system of vision comprises a device 30 adapted to provide the adapted electric field.

For example, the layer is chosen from the list consisting of polymer dispersed liquid crystals (PDLC), nematic liquid crystals, or cholesteric liquid crystals.

Preferably, the layer is made of polymer dispersed liquid crystals. The polymer and liquid crystals are imprisoned in a film. The two faces of this film are covered with a transparent, electrically conducting layer. These two conducting layers are each one connected to a flat electric conductor, fixed on one on the sides of lens. These conductors make it possible to connect lens to a power supply With no applied voltage, the liquid crystals are randomly arranged in the film, resulting in scattering of light in all the directions. Lens is translucent at this time and gets desired occlusion.

When a voltage is applied to the electrodes, the electric field formed between the transparent electrodes on the lens causes the liquid crystals to align, allowing light to pass through the film with very little scattering and resulting in a transparent state. The degree of transparency can be controlled by the applied voltage. The passage of the opalin state to a transparent state is quasi instantaneous, and can be repeated.

Furthermore, the first and the second customizable ophthalmic lenses 22 can be adapted to provide optical power for visual corrections of the wearer.

Moreover, the active system of vision 20 for the wearer further comprises an identification device 32 adapted for identifying the wearer's viewing state among far vision viewing state and near vision viewing state when wearing the first and the second customizable ophthalmic lenses. Preferably, the identification device 32 adapted for identifying when the wearer's viewing state is a near vision viewing state.

A near vision viewing state is defined by a visual acuity or resolving power for objects at distances corresponding to the normal reading distance. Clinical standards vary from about 15 to 60 cm. These distances are suitable for reading a book, for reading on computer's screen and for do-it-yourself activity. Thus a near vision viewing state within the meaning of the invention is defined for viewing distances equal to or lowers than 60 cm.

A far vision viewing state is defined by a visual acuity or resolving power for objects at distances upper than 150 cm.

For example, the detection device can be disposed on a face of the first and the second customizable ophthalmic lenses facing the eye.

The identification device 32 comprises a measurement device 34 connected to a comparison device 36. The identification device 32 will be more described later.

Furthermore, the active system of vision 20 further comprises a control unit 38 comprising a processor 40 operatively connected to each of the first and the second customizable ophthalmic lenses 22 and to the identification device 32. Thus, the processor 40 is configured to receive electrical signals depending on the wearer's viewing state from said identification device 32 and particularly depending on the identification of a near-vision viewing state or a viewing state different from a near vision viewing state.

The processor 40 is configured to switch the electrically variable occultation of one of the first and the second customizable ophthalmic lenses from the first light occultation state to the second light occultation state when a near vision viewing state is identified by the identification device.

Moreover, the processor is configured to control the electrically variable occultation of the first and the second customizable ophthalmic lenses such that they are in the first light occultation state when a viewing state different from a near vision viewing state is identified. Of course, within the meaning of the present invention, a near vision viewing state is a state adapted for reading activity such that do-it-yourself activity and reading on computer's screen and so for viewing distances lower than 60 cm.

In operation, the active system of vision 20 is adapted to carry out the steps of the method 50 for improving visual comfort of a wearer according to the invention. This method will be now described in reference to FIG. 3.

Figure 3:
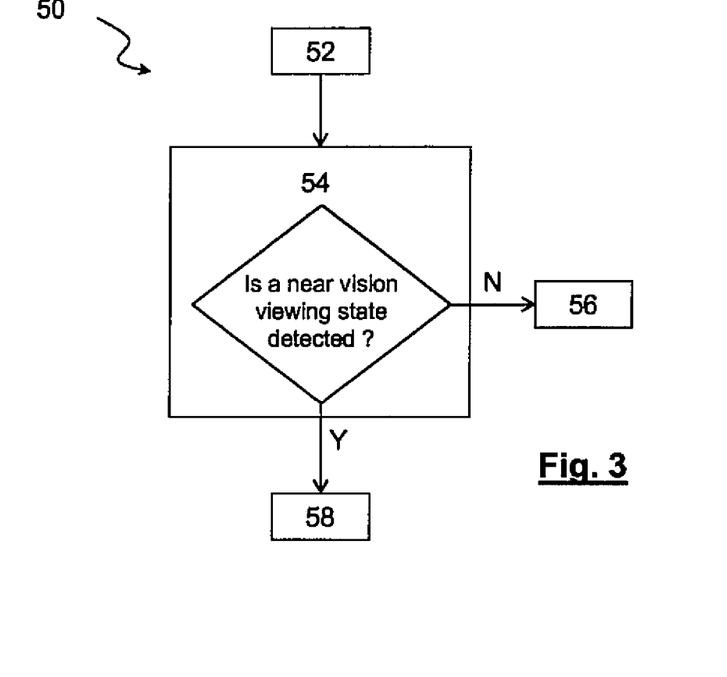
FIG. 3 is an exemplary flowchart illustrating steps of the method according to an embodiment of the invention.

This method comprises a step 52 for providing a first and a second customizable ophthalmic lenses 22 mounted on a spectacle frame as described before.

The method further comprises a step 54 for identifying the wearer's viewing state among at least a far vision viewing state and near vision viewing state.

Then, when a near vision viewing state is identified, the electrically variable occultation of one of the first and the second customizable ophthalmic lenses is switched from the first light occultation state to the second light occultation state in 56.

When the wearer's viewing state is identified as being different from said near vision viewing state, the first and the second customizable ophthalmic lenses are provided such that each of their electrically variable occultation is in the first light occultation state in 58.

Figure 4:
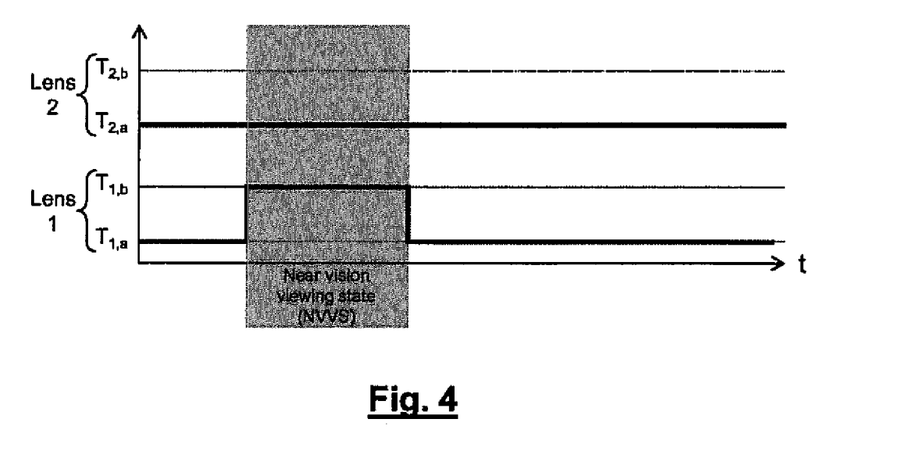
FIGS. 4 to 6 are exemplary timing diagrams representing a set of signals controlling each lens of the active system of vision of FIG. 2 according different embodiments of the method carried out by the active system.

An example of a timing diagram is illustrated on FIG. 4. Before the identification of a near vision viewing state, noted NVVS, both lenses 1 and 2 have their electrically variable occultation is in the first light occultation state $T_{1,a}$ and $T_{2,a}$. None of the eyes of the wearer are occluded.

When the near vision viewing state is identified, one lens noted lens 1 has its variable occultation switched from the first light occultation state $T_{1,a}$ to the second light occultation state $T_{1,b}$. Only the eye covered by lens 1 is occluded.

When the near vision viewing state is finished, the variable occultation of lens 1 is switched from the second light occultation state $T_{1,b}$ to the first light occultation state $T_{1,a}$. None of the eyes of the wearer are occluded.

According to a second embodiment of the method compatible with the previous one, the method further comprises a step for identifying which one of the first and the second customizable ophthalmic lenses 22 has its electrically variable occultation switched from the first light occultation state to the second light occultation state.

Moreover, the method comprises a step for switching the electrically variable occultation of the other lens from the first light occultation state to the second light occultation state when a further near vision viewing state is identified.

To achieve this, the processor 40 of the control unit 38 is adapted to identify which one of the first and the second customizable ophthalmic lenses 22 has its electrically variable occultation switched from the first light occultation state to the second light occultation state.

Furthermore, the control unit 38 comprises a memory 60 adapted to store which one of the first and the second customizable ophthalmic lenses 22 has its electrically variable occultation switched from the first light occultation state to the second light occultation state.

Figure 5:
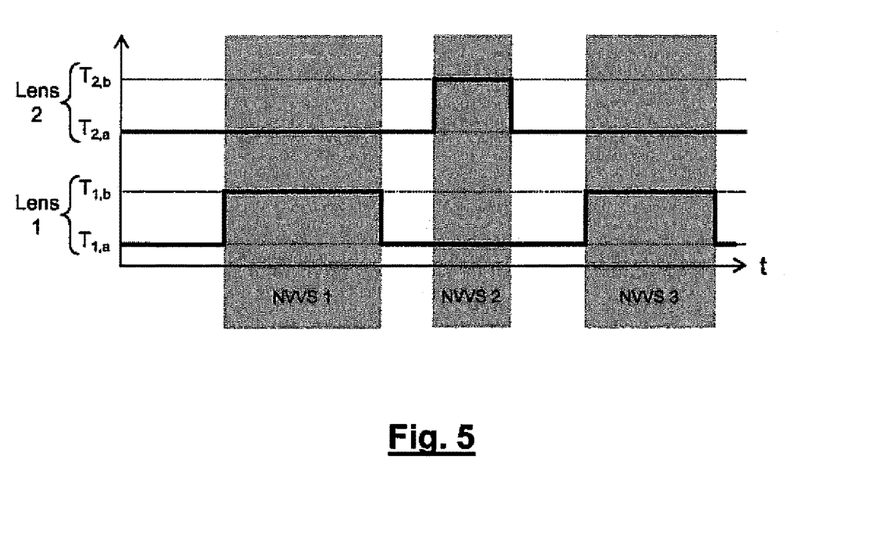

An example of a timing diagram illustrating this embodiment is shown on FIG. 5.

Before the identification of a first near vision viewing state, noted NVVS 1, both lenses 1 and 2 have their electrically variable occultation is in the first light occultation state $T_{1,a}$ and $T_{2,a}$. None of the eyes of the wearer are occluded.

When the near vision viewing state NVVS1 is identified, the lens noted lens 1 has its variable occultation switched from the first light occultation state $T_{1,a}$ to the second light occultation state $T_{1,b}$. Only the eye covered by lens 1 is occluded during NVVS1. Information corresponding to the "occlusion" switch of lens 1 is stored in the memory.

When the near vision viewing state NVVS1 is finished, the variable occultation of lens 1 is switched from the second light occultation state $T_{1,b}$ to the first light occultation state $T_{1,a}$. None of the eyes of the wearer are occluded.

When a second near vision viewing state noted NVVS2 is identified, the processor read in the memory which one of the lenses has been lastly switched, i.e. lens 1 in the example. Then the lens noted lens 2 has its variable occultation switched from the first light occultation state $T_{2,a}$ to the second light occultation state $T_{2,b}$. Only the eye covered by lens 2 is occluded during NVVS2. Information corresponding to the "occlusion" switch of lens 2 is stored in the memory.

When the near vision viewing state NVVS2 is finished, the variable occultation of lens 2 is switched from the second light occultation state $T_{2,b}$ to the first light occultation state $T_{2,a}$. None of the eyes of the wearer are occluded.

When a third near vision viewing state noted NVVS3 is identified, the processor read in the memory which one of the lenses has been lastly switched, i.e. lens 2 in the example. Then the lens noted lens 1 has its variable occultation switched from the first light occultation state $T_{1,a}$ to the second light occultation state $T_{1,b}$. Only the eye covered by lens 1 is occluded during NVVS3. Information corresponding to the "occlusion" switch of lens 1 is stored in the memory.

Thanks to this embodiment, it is possible to alternate which eye is occluded during the near vision viewing states in order to not always occlude the same eye and so to make one eye stronger and the other one weaker.

According to a third embodiment of the method compatible with the previous ones, the method further comprises a step for providing a switching time period when a near vision viewing state is identified.

Then during the identification of the near vision viewing state, the electrically variable occultation of the first and the second customizable ophthalmic lenses are switched alternatively after each switching time period from the first light occultation state to the second light occultation state during a near vision viewing state. The switching time period can be constant or not.

For example, during a reading state, the electrically variable occultation of the first and the second customizable ophthalmic lenses can be switched alternatively after each page, i.e. after each vertical ocular saccades for the eyes if they are detected by the identification device 32.

To achieve this, the processor 40 is configured to switch the electrically variable occultation of the first and the second customizable ophthalmic lenses alternatively after each switching time period from the first light occultation state to the second light occultation state during a near vision viewing state.

Thanks to this embodiment, it is possible to alternate which eye is occluded during the near vision viewing states in order to not always occlude the same eye and so to make one eye stronger and the other one weaker.

Figure 6:
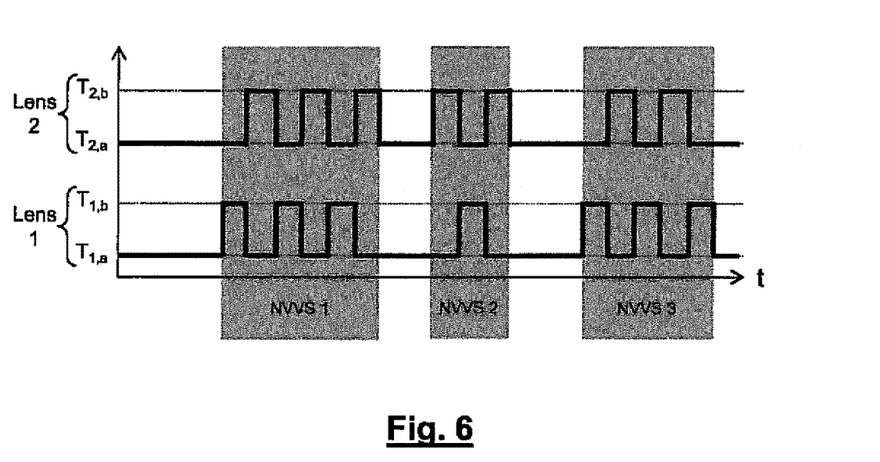

An example of a timing diagram illustrating this embodiment is shown on FIG. 6.

Before the identification of a first near vision viewing state, noted NVVS 1, both lenses 1 and 2 have their electrically variable occultation is in the first light occultation state $T_{1,a}$ and $T_{2,a}$. None of the eyes of the wearer are occluded.

When the near vision viewing state NVVS1 is identified, one of the lenses, noted lens 1 in the example shown on FIG. 6, has its variable occultation switched from the first light occultation state $T_{1,a}$ to the second light occultation state $T_{1,b}$.

Then, for example at the detection of a vertical saccade of the eyes, lens 1 and lens 2 have their variable occultation alternatively and out-of-phase switched from one light occultation state $T_{i,n}$ (i={1, 2} and n={a, b}) to the other light occultation state $T_{i,m}$ (i={1, 2} and n={a, b}). The eyes are so alternatively occluded during the near vision viewing state NVVS1.

When the near vision viewing state NVVS1 is finished, the variable occultation of the lens covering the last occluded eye, noted lens 2 in the example shown on FIG. 6, is switched from the second light occultation state $T_{2,b}$ to the first light occultation state $T_{2,a}$. None of the eyes of the wearer are occluded.

According to a first embodiment of the active system of vision, the measurement device 34 of the identification device 32 is adapted to measure an oculo-motor activity of each eye of the wearer.

Furthermore, the comparison device 36 of the identification device is adapted to compare the measured oculo-motor activity of each eye of the wearer with standard oculo-motor activity of each eye during a near vision viewing state.

Particularly, the measurement device is adapted to determine for each eye, the actual gaze direction ($\alpha_a$, $\beta_a$) of the eye of the wearer when wearing the first and the second customizable ophthalmic lenses.

For example and preferably, the actual gaze direction ($\alpha_a$, $\beta_a$) of the eye of the wearer is determined by tracking the pupil of the eye of the wearer thanks to an eye-tracker device.

For example, said measurement device is adapted to characterize the direction of gaze of a wearer according to WO 2010/130932 A1.

Moreover, the processor 40 is configured to receive electrical signals depending on the actual gaze direction of the eye from the identification device 32.

In operation, during the step for identifying the wearer's viewing state by the identification device, the actual gaze direction of the eye of the wearer is determined for each eye when wearing the first and the second customizable ophthalmic lenses.

Moreover, the number and magnitude of ocular saccades can be detected for each eye from the actual gaze directions of the eyes of the wearer.

Then, for each eye the actual number and magnitude of ocular saccades of the eyes of the wearer can be compared with standard number and magnitude of ocular saccades during a near vision viewing state.

It is sufficient to determine only the number and magnitude of horizontal ocular saccades.

According to a subembodiment, the measurement device is adapted to determine a convergence of the eyes of the wearer from the actual gaze directions of the eyes of the wearer according to WO 2010/130931 A1.

Moreover, the processor 40 is configured to receive electrical signals depending on the actual convergence of the eyes from the identification device 32.

Moreover, the comparison device is adapted to compare the actual convergence of the eyes of the wearer with a standard viewing convergence of the eyes during a near vision viewing state. Standard viewing convergence of the eyes during a near vision viewing state within the meaning of the invention varies usually between 2.5° and 12°. Of course, an identification of a near vision viewing state based on at least several parameters among the convergence of the eyes, number and magnitude of ocular saccades of the eyes and gaze direction of the eyes of the wearer is more robust.

According to a second embodiment of the active system of vision, the measurement device of the identification device is adapted to measure the actual viewing distance of the eye of the wearer when wearing the customizable ophthalmic lens. For example, the measurement device comprises a telemeter.

Furthermore, the processor 40 is configured to receive electrical signals depending on the actual viewing distance of the eye from the identification device 32.

Moreover, the comparison device of the identification device is adapted to compare the actual viewing distance of the wearer with a standard viewing distance during a near vision viewing state. Standard viewing a standard viewing distance during a near vision viewing state within the meaning of the invention varies usually between 15 cm and 60 cm. Of course, the second embodiment of the active system of vision is compatible with the first embodiment. Indeed, an identification of a near vision viewing state based on oculo-motor activity measurement and viewing distance measurement would be more robust.

According to a third embodiment of the active system of vision, the measurement device of the identification device is adapted to measure the actual inclination of the head of the wearer when wearing the customizable ophthalmic lens. For example, the measurement device comprises a gyroscope.

Furthermore, the processor 40 is configured to receive electrical signals depending on the actual inclination of the head from the identification device 32.

Moreover, the comparison device of the identification device is adapted to compare the actual inclination of the head of the wearer with a standard viewing inclination of the head during a near vision viewing state. Standard viewing inclination of the head during a near vision viewing state within the meaning of the invention varies usually between 20° and 70°. Preferably, standard viewing inclination of the head during a reading vision viewing state varies usually between 50° and 55° for non-presbyopic wearers and between 35° and 40° for presbyopic wearers. Of course, the second embodiment of the active system of vision is compatible with the previous one. Indeed, an identification of a near vision viewing state based on at least two parameters among oculo-motor activity measurement, viewing distance measurement and measurement of the inclination of the head would be more robust.

According to a fourth embodiment compatible with the previous ones, each of the first and the second customizable ophthalmic lenses further comprises a transparent set of electroactive cells juxtaposed preferably parallel to a surface of the said customizable ophthalmic lens such as in pixelated lenses.

Said set of cells is suitable for providing an optical phase-shift distribution function with a substantially constant value within each cell. The optical phase-shift distribution is associated to the electrically variable occultation of said customizable ophthalmic lens.

It is known to use substances having specific optical properties to make active transparent optical elements. These substances cooperate to give optical characteristics required for a particular application to the optical component.

For example, transparent substances having different refraction index can be divided in a set of juxtaposed cells forming the transparent substrate, so that the resulting component is a draft of lens adapted to correct visual defects. The optical properties regarding how the wavefront is modified by the optical element, also called the "dioptric function", result in the optical combination of the transparent substrate and of the set of juxtaposed cells. For example, for the corrective lens application, it is advisable for different cells of the optical element to contain substances of varying refraction index such that the refraction index is adapted to vary along the surface of the optical element, according to the estimated ametropy of an eye to be corrected.

Moreover, such a transparent optical element can also have various additional optical functions, such as light absorption, polarizing capability, reinforcement of contrast capability, etc. . . . .

Preferably, each cell 26 is filled with an active electromaterial such that the refraction index can vary in each pixel independently from each other under the action of an electric field induced by individual electrodes 28.

Of course, the device 30 of the active system of vision is adapted to provide the adapted electric field.

Furthermore, the processor is configured to calculate a modified phase-shift distribution function for each customizable ophthalmic lens such that the modified phase-shift distribution function is associated to the second light occultation state of the electrically variable occultation.

Moreover, the processor is configured to activate each electroactive cells according to the said modified phase-shift distribution function.

In operation, the active system of vision carry out the steps of a method according to the invention, as described before. This method further comprises a step for providing a reference phase-shift distribution function adapted to provide to the wearer a given dioptric function $DF(\alpha, \beta)$ to each customizable ophthalmic lens. This dioptric function was pre-calculated in order to correct visual defects of the wearer. A reference phase-shift distribution function has then be calculated to provide to the wearer a given dioptric function $DF(\alpha, \beta)$. Each electroactive cell is then activated according to the said calculated phase-shift distribution function and to the first or the second light occultation state.

Thanks to this additional given dioptric function, it is possible to provide optical power for visual corrections of the wearer which can be different in near vision and in far vision. The invention applies in the same manner for pixelated lenses associated with the correction of defects of astigmatism or other visual defects.

Furthermore, the invention also relates to a computer program product comprising one or more stored sequence of instructions that is accessible to a processor and which, when executed by the processor, causes the processor to carry out the steps of the different embodiments of the preceding methods.

The invention also proposes a computer readable medium carrying out one or more sequences of instructions of the preceding computer program product.

Unless specifically stated otherwise, as apparent from the following discussions, it is appreciated that throughout the specification discussions utilizing terms such as "evaluating", "computing", "calculating" "generating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

It should be noted more generally that the invention is not limited to the described and represented examples.

In particular, the invention applies in the same manner for pixelated lenses associated with the correction of defects of astigmatism or other visual defects.

The invention makes it possible to improve binocular vision for the wearer in near vision.

The invention claimed is:

1. A method for improving visual comfort to a wearer and for improving binocular vision for the wearer in near vision, comprising the following:
   providing a first and a second customizable ophthalmic lenses mounted on a spectacle frame, the first customizable ophthalmic lens to be disposed in front of one eye of the wearer and the second customizable ophthalmic lens to be disposed in front of the other eye of the wearer, each lens having an electrically variable occultation between a first light occultation state and a second light occultation state, the first light occultation state being substantially transparent and the second light occultation state being substantially obscured;
   identifying the wearer's viewing state among at least a near vision viewing state (NVVS), the near vision viewing state being defined for viewing distances equal to or lower than 60 cm, wherein identifying the wearer's viewing state comprises:
      measuring an oculo-motor activity of each eye of the wearer and comparing measured oculo-motor activity of each eye of the wearer with standard oculo-motor activity of each eye during the near vision viewing state;
      determining, for each eye, an actual gaze direction of the eye of the wearer when wearing the first and the second customizable ophthalmic lenses;
      determining an actual number and magnitude of horizontal ocular saccades for each eye from the actual gaze directions of the eyes of the wearer; and
      comparing the actual number and magnitude of horizontal ocular saccades of the eyes of the wearer with standard number and magnitude of ocular saccades during the near vision viewing state;
   switching the electrically variable occultation of one of the first and the second customizable ophthalmic lenses from the first light occultation state to the second light occultation state when the near vision viewing state (NVVS) is identified while at the same time the other lens is in the transparent state; and
   providing the first and the second customizable ophthalmic lenses such that each of their electrically variable occultation is in the first light occultation state when the wearer's viewing state is identified as being different from said near vision viewing state.

2. The method for improving visual comfort of a wearer according to claim 1, wherein the method further comprises the following:
   identifying which one of the first and the second customizable ophthalmic lenses has its electrically variable occultation switched from the first light occultation state to the second light occultation state; and
   switching the electrically variable occultation of the other lens from the first light occultation state to the second light occultation state when a further near vision viewing state is identified.

3. The method for improving visual comfort of a wearer according to claim 1, wherein the method further comprises the following when a near vision viewing state is identified:
   providing a switching time period; and
   switching alternatively after each switching time period, the electrically variable occultation of the first and the second customizable ophthalmic lenses from the first light occultation state to the second light occultation state during a near vision viewing state.

4. The method for improving visual comfort of a wearer according to claim 1, wherein the identifying the wearer's viewing state comprises:
   determining, for each eye, the actual gaze direction of the eye of the wearer when wearing the first and the second customizable ophthalmic lenses;
   determining a convergence of the eyes of the wearer from the actual gaze directions of the eyes of the wearer; and
   comparing the actual convergence of the eyes of the wearer with a standard viewing convergence of the eye during a near vision viewing state.

5. The method for improving visual comfort of a wearer according to claim 1, wherein the identifying the wearer's viewing state comprises measuring the actual viewing distance of the eye of the wearer when wearing the customizable ophthalmic lens, and comparing the actual viewing distance of the eye of the wearer with a standard viewing distance of the eye during a near vision viewing state.

6. The method for improving visual comfort of a wearer according to claim 1, wherein the identifying the wearer's viewing state comprises measuring the actual inclination of the head of the wearer when wearing the customizable ophthalmic lens, and comparing the actual inclination of the head of the wearer with a standard viewing inclination of the head during a near vision viewing state.

7. A non-transitory computer program product comprising one or more stored sequences of instructions that is accessible to a processor and which, when executed by the processor, causes the processor to carry out claim 1.

8. A non-transitory computer readable medium storing one or more sequences of instructions of the computer program product of claim 7.

9. The method for improving visual comfort of a wearer according to claim 1, wherein the actual number and magnitude of only horizontal ocular saccades is determined for each eye from the actual gaze directions of the eyes of the wearer.

10. An active system of vision for a wearer and for improving binocular vision for the wearer in near vision, comprising:
   a first and a second customizable ophthalmic lenses mounted on a spectacle frame, the first customizable ophthalmic lens to be disposed in front of one eye of the wearer and the second customizable ophthalmic lens to be disposed in front of the other eye of the wearer, each lens having an electrically variable occultation between a first light occultation state and a second light occultation state, the first light occultation state being substantially transparent and the second light occultation state being substantially obscured;
   an identification circuitry to identify the wearer's viewing state among at least a near vision viewing state when wearing the first and the second customizable ophthalmic lenses, a near vision viewing state being defined for viewing distances equal to or lower than 60 cm, wherein the identification circuitry is configured to:
      measure an oculo-motor activity of each eye of the wearer and comparing measured oculo-motor activity of each eye of the wearer with standard oculo-motor activity of each eye during a near vision viewing state;

determine, for each eye, an actual gaze direction of the eye of the wearer when wearing the first and the second customizable ophthalmic lenses;

determine an actual number and magnitude of horizontal ocular saccades for each eye from the actual gaze directions of the eyes of the wearer; and compare the actual number and magnitude of horizontal ocular saccades of the eyes of the wearer with standard number and magnitude of ocular saccades during a near vision viewing state; and a circuitry operatively connected to each of the first and the second customizable ophthalmic lenses and to the identification device, wherein the circuitry is configured to:

switch the electrically variable occultation of one of the first and the second customizable ophthalmic lenses from the first light occultation state to the second light occultation state when a near vision viewing state (NVVS) is identified by the identification device while at the same time the other lens is in the transparent state; and control the electrically variable occultation of the first and the second customizable ophthalmic lenses such that they are in the first light occultation state when the wearer's viewing state is identified as being different from a near vision viewing state (NVVS) by the identification device.

11. The active system of vision for a wearer according to claim 10, wherein the first and the second customizable ophthalmic lenses having an electrically variable occultation comprise a layer chosen from the list consisting of polymer dispersed liquid crystals, nematic liquid crystals, or cholesteric liquid crystals.

12. The active system of vision for a wearer according to claim 10, wherein each of the first and the second customizable ophthalmic lenses comprises a transparent set of electroactive cells juxtaposed parallel to a surface of the said customizable ophthalmic lens, said set of cells to provide an optical phase-shift distribution function with a constant value within each cell, the optical phase-shift distribution being associated to the electrically variable occultation of said customizable ophthalmic lens and wherein the circuitry is configured to:

calculate a modified phase-shift distribution function for each customizable ophthalmic lens such that the modified phase-shift distribution function is associated to the second light occultation state of the electrically variable spectral occultation; and activate each electroactive cells according to the said modified phase-shift distribution function.

13. The active system of vision for a wearer according to claim 10, wherein the actual number and magnitude of only horizontal ocular saccades is determined for each eye from the actual gaze directions of the eyes of the wearer.

14. The active system of vision for a wearer according to claim 10, wherein the system is confined to the spectacle frame.

* * * * *